US009055896B2

(12) United States Patent
Amthor et al.

(10) Patent No.: US 9,055,896 B2
(45) Date of Patent: Jun. 16, 2015

(54) OPHTHALMOSCOPE FOR OBSERVING AN EYE

(75) Inventors: Kay-Uwe Amthor, Potsdam (DE); Ben Liesfeld, Potsdam (DE)

(73) Assignee: OD-OS GmbH, Teltow/Berlin (DE)

( * ) Notice: Subject to any disclaimer, the term of this patent is extended or adjusted under 35 U.S.C. 154(b) by 373 days.

(21) Appl. No.: 13/497,493

(22) PCT Filed: Sep. 29, 2010

(86) PCT No.: PCT/EP2010/006037
§ 371 (c)(1),
(2), (4) Date: Jul. 20, 2012

(87) PCT Pub. No.: WO2011/038937
PCT Pub. Date: Apr. 7, 2011

(65) Prior Publication Data
US 2012/0274901 A1 Nov. 1, 2012

Related U.S. Application Data

(60) Provisional application No. 61/246,745, filed on Sep. 29, 2009.

(30) Foreign Application Priority Data

Sep. 29, 2009 (EP) .................................... 09075450

(51) Int. Cl.
*A61B 3/14* (2006.01)
*A61B 3/12* (2006.01)
*A61F 9/008* (2006.01)

(52) U.S. Cl.
CPC .................. *A61B 3/12* (2013.01); *A61B 3/1241* (2013.01); *A61F 9/008* (2013.01); *A61F 2009/00863* (2013.01)

(58) Field of Classification Search
CPC ........... A61B 3/12; A61B 3/1241; A61B 3/13
USPC .......................... 351/204, 205, 206, 214, 246
See application file for complete search history.

(56) References Cited

U.S. PATENT DOCUMENTS 4,248,505 A * 2/1981 Muchel et al. ................ 351/206
4,452,517 A   6/1984 Kohayakawa
(Continued)

FOREIGN PATENT DOCUMENTS

DE    3001244 A1    7/1980
EP    0791361 A2    8/1997
(Continued)

OTHER PUBLICATIONS

European Search Report issued in EP Application No. 06116853, dated Apr. 24, 2007.
(Continued)

*Primary Examiner* — Huy K Mai
(74) *Attorney, Agent, or Firm* — Faegre Baker Daniels LLP (57) ABSTRACT

An ophthalmoscope for observing an eye comprises a converging first lens system for generating a real intermediate image of a region in the eye in an intermediate image plane as well as an observation apparatus having an imaging optics for imaging the real intermediate image in an imaging plane in the observation apparatus and for imaging an aperture of the observation apparatus in a pupil of the eye. Between the first lens system and the imaging optics of the observation apparatus, a diverging second lens system is provided for enlarging a working distance between the first lens system and the pupil and for enlarging a field angle.

22 Claims, 4 Drawing Sheets (56) References Cited

U.S. PATENT DOCUMENTS

| | | | |
|---|---|---|---|
| 4,666,268 A | 5/1987 | Ito | |
| 5,430,506 A * | 7/1995 | Volk | 351/205 |
| 5,526,189 A | 6/1996 | Heacock | |
| 5,912,720 A | 6/1999 | Berger et al. | |
| 6,159,202 A | 12/2000 | Sumiya et al. | |
| 6,247,812 B1 | 6/2001 | Moore et al. | |
| 6,758,564 B2 | 7/2004 | Ferguson | |
| 8,100,531 B2 | 1/2012 | Liesfeld et al. | |
| 8,545,020 B2 | 10/2013 | Liesfeld et al. | |
| 8,545,021 B2 | 10/2013 | Liesfeld et al. | |
| 8,545,022 B2 | 10/2013 | Liesfeld et al. | |
| 2001/0005225 A1 | 6/2001 | Clark et al. | |
| 2002/0099363 A1 | 7/2002 | Woodward et al. | |
| 2003/0208189 A1 | 11/2003 | Payman | |
| 2005/0105044 A1 | 5/2005 | Warden et al. | |
| 2006/0114544 A1 | 6/2006 | Bloom et al. | |
| 2007/0055222 A1 | 3/2007 | Hohla et al. | |
| 2007/0216909 A1 | 9/2007 | Everett et al. | |
| 2008/0165322 A1 | 7/2008 | Su et al. | |
| 2008/0278683 A1 | 11/2008 | Su et al. | |
| 2009/0244482 A1 | 10/2009 | Elsner et al. | |
| 2010/0007849 A1 | 1/2010 | Liesfeld et al. | |
| 2012/0089133 A1 | 4/2012 | Liesfeld et al. | |
| 2012/0165905 A1 | 6/2012 | Liesfeld et al. | |
| 2012/0165906 A1 | 6/2012 | Liesfeld et al. | |
| 2012/0239015 A1 | 9/2012 | Liesfeld et al. | |

FOREIGN PATENT DOCUMENTS

| | | |
|---|---|---|
| EP | 1389943 A2 | 2/2004 |
| WO | WO9101703 A1 | 2/1991 |
| WO | WO9905853 A1 | 2/1999 |
| WO | WO0195791 A1 | 10/2001 |
| WO | WO02094088 A2 | 11/2002 |

OTHER PUBLICATIONS

European Search Report issued in EP Application No. 09075449, Dated Jan. 26, 2010.
European Search Report issued in EP Application No. 09075450, mailed Feb. 8, 2010.
International Search Report and Written Opinion issued in PCT/EP2007/056967 mailed Jan. 29, 2008.
International Search Report and Written Opinion issued in PCT/EP2010/006031, mailed Mar. 10, 2001.
International Search Report and Written Opinion issued in PCT/EP2010/006037, mailed May 11, 2010, 14 pages.
Kaiser, Richard S. et al., "Laser Burn Intensity and the risk for Choroidal Neovascularization in the CNVPT Fellow Eye Study", Ophtalmologie, Paris; vol. 119, Jun. 1, 2001, pp. 826-832.
Parel, Jean-Marie et al., "Review Article: The Optics of the Ophthalmoscope and Related Instruments", Journal of Physics E. Scientific Instruments, vol. 13, No. 12, Dec. 1, 1980, pp. 1242-1253.
Yannuzzi, L.A. et al., "Ophthalmic fundus imaging: today and beyond", American Journal of Ophthalmology, vol. 137, No. 3, Mar. 1, 2004, pp. 511-524.

* cited by examiner

OPHTHALMOSCOPE FOR OBSERVING AN EYE

CROSS-REFERENCE TO RELATED APPLICATION

This application claims priority to PCT Patent Application No. PCT/EP2010/006037, filed Sep. 29, 2010, which claims priority to U.S. Provisional Application No. 61/246,745, filed Sep. 29, 2009, and European Patent Application No. 09075450.8, filed Sep. 29, 2009, which are herein incorporated by reference in their entirety.

TECHNICAL FIELD

The invention relates to an ophthalmoscope for observing an eye and a method of observing an eye.

BACKGROUND

The observation of an eye, particularly of a fundus of the eye, usually serves for making a diagnosis of diseases of the eye as well as for the treatment of such diseases. In particular, age-related macular degeneration or diabetic retinopathy belong to these diseases. An early recognition of these diseases by diagnostic methods such as direct observation of the retina by a physician, fundus images, fluorescence images or optical coherence tomographies need special optical technologies since the fundus of the eye must be observed and imaged through a small opening of an eye pupil, respectively.

For the treatment of diseases of the retina frequently a laser irradiation is carried out on symptomatic regions of the retina. For this treatment a laser radiation must be coupled into the eye through the eye pupil and focused on the location to be radiated. During such a treatment the observation of the retina is necessary, as well.

Optical elements used directly at the eye for this purpose play a decisive role for the accuracy of an optical image of the fundus of the eye. For the observation of the fundus of the eye a slit lamp is used by standard. Using an ophthalmoscoping lens as explained for example in U.S. Pat. No. 5,526,189 the fundus of the eye is imaged in an intermediate image plane. This intermediate image plane is viewed with a stereo microscope. The illumination of the fundus of the eye is carried out by a slit illumination which is coupled into the eye via the ophthalmoscoping lens. Critical disadvantages of such a fundus observation by means of a slit lamp, on the one hand, is a restriction toward a slit-shaped field of view on the retina as well as reflections of the illumination on the ophthalmoscoping lens and on a cornea of the patient which overlay the image of the fundus as interfering artefacts.

Furthermore, for the documentation of an examination or a treatment, respectively, it is necessary to store images of the fundus of the eye. To this end, for example fundus cameras and indirect ophthalmoscopes, respectively are used. In doing so, a converging lens system of the ophthalmoscope creates an intermediate image of the fundus of the eye which is imaged in an imaging plane by an imaging optics provided downstream, and in this imaging plane mostly an electronic photosensitive sensor is arranged.

With the observation of the fundus of the eye with an indirect ophthalmoscope the following parameters and boundary conditions are relevant. A field angle which is characterized by a maximum angle that two light beams starting from the eye and being imageable in the imaging plane by means of the ophthalmoscope may enclose between them, which should be as large as possible to allow a visual field of the fundus of the eye as large as possible, a size of the light sensitive sensor, and a construction size of the imaging optics of the ophthalmoscope which should be as compact as possible to keep the distance between the physician and the patient to be treated as small as possible (smaller than an arm length). In addition, relevant parameters are an imaging quality as high as possible, a diameter of the pupil of the examined eye which is smaller than 4 mm as a rule upon a preferably non-mydriatic examination, a working distance between the ophthalmoscope and the eye defined by a distance between the cornea of the eye and a surface of an entrance lens of the ophthalmoscope facing the eye which should be as large as possible so that other optical elements can be placed between the ophthalmoscope and the eye without any problems, and furthermore a larger distance between the ophthalmoscope and the nose and forehead of a patient is achieved to obtain a greater freedom of movement for the ophthalmoscope. The mentioned requirements are closely interconnected so that changes of one of these parameters have effects on the other parameters.

For example, selecting a cost-effective sensor having a diagonal of about 0.5 inch or smaller, then an intermediate image of the fundus of the eye must be usually imaged highly reduced in size onto this sensor. This either necessitates a great construction length of the imaging optics by which the distance between the physician and the patient is enlarged or the use of optical elements having short focal distances which however are in conflict with achieving a high imaging quality. To achieve a working distance as large as possible one may select an objective of the ophthalmoscope having a large focal distance. However, since the size of the intermediate image also scales with the focal distance of the objective the larger intermediate image is no longer completely detectable by the sensor with unchanged optics provided downstream. Thus, either a larger sensor has to be selected which highly enhances costs of the ophthalmoscope, or the optics provided downstream in turn as described must be able to achieve a severe reduction in size of the intermediate image which either requires a longer form of construction or the use of heavily refracting optical elements including the disadvantages mentioned above.

In addition to the creation of an intermediate image it is the object of the objective of an ophthalmoscope to allow a Maxwellian illumination upon which an apparatus pupil which usually is given by an aperture of the imaging optics is imaged into the pupil of the eye to be examined Maxwellian illumination, also referred to as pupil imaging, allows the spatial separation of an observation beam path and an illumination beam path on the cornea of the eye in the vicinity of the pupil of the eye. By this spatial separation of the mentioned beam paths it is guaranteed that reflections on the cornea of the eye and on surfaces of the objective in the fundus image do not superimpose the reflection from the fundus of the eye, i.e. the observation beam which carries the decisive image information from the eye. Furthermore, the pupil imaging allows a particularly large field angle since a particularly large region of the eye may be imaged on the sensor of the ophthalmoscope. However, pupil imaging requires an accurately adjusted working distance. If the ophthalmoscope is positioned too far from the eye the aperture is imaged in front of the eye outside of the pupil. By this, the field angle is reduced, and moreover amounts of stray light will not be removed from the observation beam path as described above.

SUMMARY OF THE INVENTION

In one aspect, an ophthalmoscope for observing an eye includes a converging first lens system configured to generate a real intermediate image of a region in the eye in an intermediate image plane. The ophthalmoscope also includes an observation apparatus having imaging optics configured to image the real intermediate image in an imaging plane in the observation apparatus and configured to image an aperture of the observation apparatus in a pupil of the eye. The ophthalmoscope further includes a diverging second lens system between the first lens system and the imaging optics of the observation apparatus. The diverging second lens system configured to enlarge a working distance between the first lens system and the pupil and to enlarge a field angle.

In another aspect, a method for observing an eye with an ophthalmoscope includes reflecting an observation beam in the eye to generate an intermediate image of a region in the eye in an intermediate image plane with a first lens system. The method also includes imaging, with an observation apparatus having imaging optics, the intermediate image in an imaging plane in the observation apparatus. The method further includes diverging the observation beam in a beam path between the first lens system and the imaging optics by a second lens system, and imaging an aperture of the observation apparatus in a pupil of the eye.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
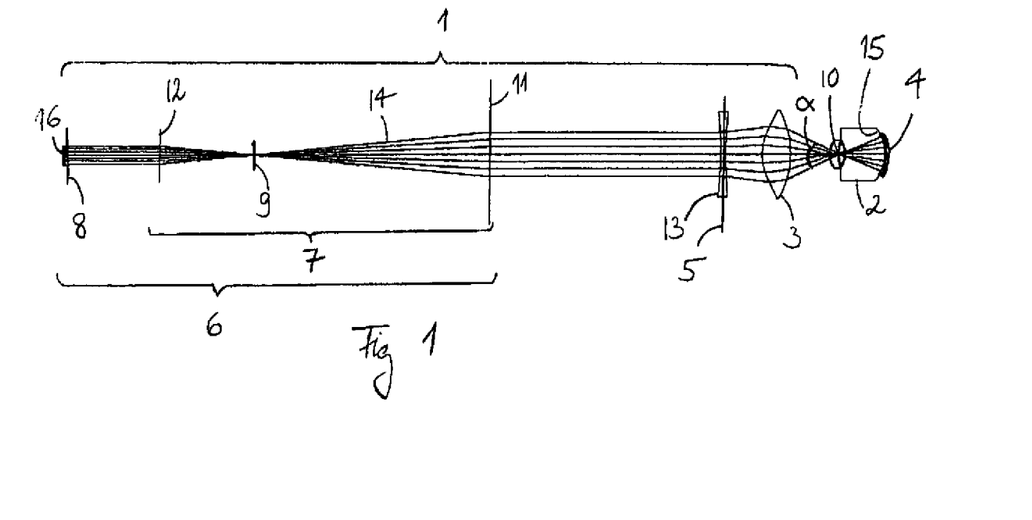
FIG. 1 shows imaging of a fundus of an eye by means of an ophthalmoscope of the type proposed herein.

FIG. 1 shows a schematic representation of a specific embodiment of an ophthalmoscope 1 of the type proposed herein for observing an eye 2. The ophthalmoscope 1 comprises a converging first lens system 3 for generating a real intermediate image 5 of a region 4 in the eye in an intermediate image plane 5 as well as an observation apparatus 6 having an imaging optics 7 for imaging the real intermediate image 5 in an imaging plane 8 inside of the observation apparatus 6 and for imaging an aperture 9 of the observation apparatus 6 in a pupil of the eye 4. The imaging optics 7 in this specific embodiment includes two converging lenses 11, 12. For achieving a higher imaging quality, in more complex embodiments instead of the single lenses 11 and 12 respective lens systems are provided which may comprise a number of lenses.

Further the ophthalmoscope comprises a diverging second lens system 13 wherein the intermediate image plane 5 runs inside of this second lens system 13. In the embodiment represented herein the second lens system 13 comprises one single diverging lens 13.

The beam path schematically shown in FIG. 1 serves for the illustration of a pupil imaging, i.e. the imaging of the aperture 9 onto the eye pupil 10 wherein one divergent beam of rays 14 starting from the aperture 9 is focused on the pupil 10. An especially large region 4 in the eye is illuminated and observed, respectively, by the pupil imaging. A size of the region 4 immediately corresponds to a large field angle α. In the embodiment represented herein the field angle is 50° which corresponds to a region 4 having a diameter of about 16 mm on a fundus 15 of the eye.

In this embodiment the first converging lens system 3 contains one single converging lens 3 which so represents the entrance lens of the ophthalmoscope 1 which is shaped aspherically for improving the imaging characteristics of the ophthalmoscope under large observation angles (field angles) α. The ophthalmoscope 1 further comprises a light sensitive sensor 16 which is arranged in the imaging plane 8 for generating electric image signals. Further the ophthalmoscope comprises a digital image processing unit (not shown herein) for carrying out image processing functions.

Figure 2:
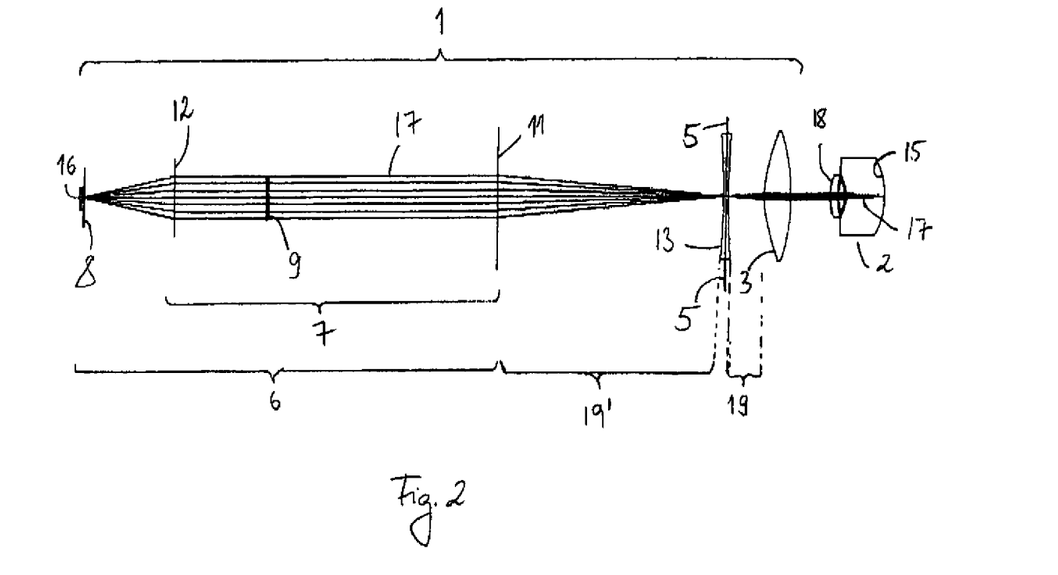
FIG. 2 shows pupil imaging by means of an ophthalmoscope of the type proposed herein.

In FIG. 2 the exemplary ophthalmoscope 1 already described above according to FIG. 1 is shown once again. In FIG. 2 the situation of a fundus imaging is illustrated which is distinguished due to the fact that a beam of rays starting from the fundus 15 of the eye is imaged by the first converging lens system 3 in the intermediate image plane 5. In the further beam path this beam of rays is parallelised by the first converging lens 11 of the imaging optics 7, spatially limited by the aperture 9 (aperture diaphragm), and subsequently imaged by the second converging lens 12 in the imaging optics 7 in the imaging plane 8 onto the sensor 16.

The first lens system 2 and the second lens system 13 of the ophthalmoscope 1 described herein thus are applicable to simultaneously depict the fundus 15 of the eye 2 onto the sensor 16 of the observation apparatus 6 and to depict the aperture 9 in the pupil 10 which is located behind the cornea 18 of the eye 2 inside of the eye 2.

Moreover, by the diverging lens 13 contained in the second lens system a working distance between the first lens system and the eye 2 is enlarged as will be explained from the following figures in greater detail.

In this embodiment the intermediate image plane 5 is arranged inside of the lens system 13. In alternative embodiments the intermediate image plane (5) is located in a first interstice (19) between the first lens system (3) and the second lens system (13) or in a second interstice (19') between the second lens system (13) and the imaging optics (7).

Figure 3:
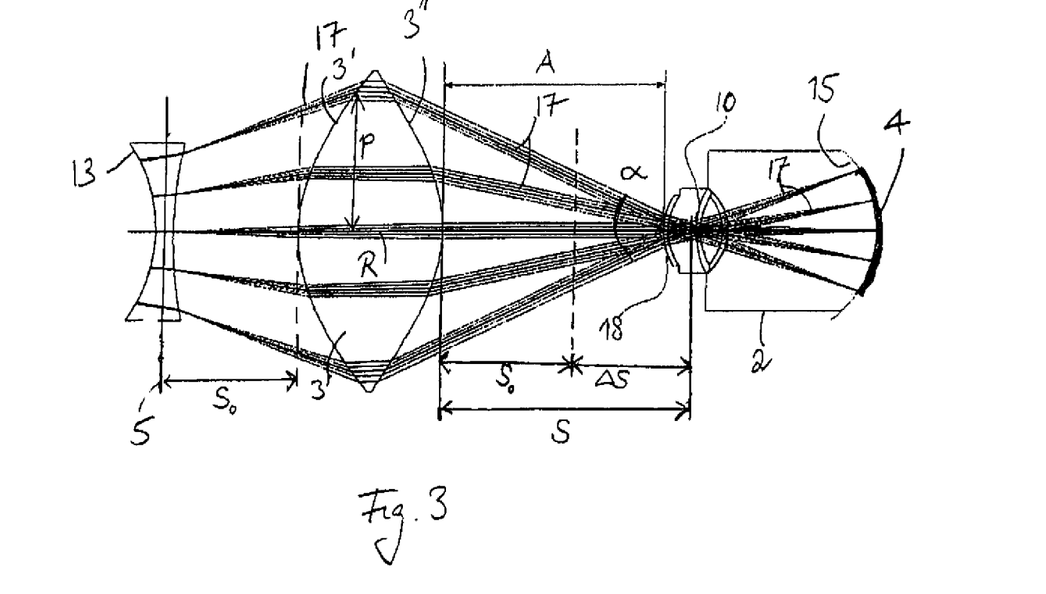
FIG. 3 shows an ophthalmoscope of the type proposed herein with an intermediate image plane inside of a lens of the second lens system.

In FIG. 3 a section of an ophthalmoscope described according to FIG. 1 and FIG. 2 is shown. In FIG. 3 the beam paths of a plurality of beams of rays 17 starting from the observed region 4 on the fundus 15 of the eye 1 are sketched in. At first, starting from the fundus 15 of the eye they pass through the pupil 10 and exit from the eye 1. Afterwards they impinge at first onto the converging lens system 3 (of the entrance lens) focusing them in the intermediate image plane 5.

The beams of rays 17 exiting from the eye 4 consist of collimated light beams such that the single beams of rays are focused by the converging lens system 3 in a focal plane 5 of the first lens system 3 being identical with the intermediate image plane 5. Thus, a distance labelled as $S_o$ between the intermediate image plane 5 and a surface 3' of the converging lens system 3 facing the intermediate image plane 5 approximately corresponds to a focal plane of the lens system 3.

Further, the converging lens 3 is shaped aspherically as already described above. In this way, even those beams of rays 17 which impinge the converging lens 3 with a large entrance height P are imaged onto the intermediate image plane 5 such that preferably the entire region 4 is optically conjugated with the intermediate image plane 5. The entrance height is defined as the distance between the entrance point of the respective beam of light and a symmetry axis R of the lens.

By the arrangement of the diverging lens 13 in the intermediate image plane 5 the working distance A between a surface 3" of the first lens system 3 facing the eye and a cornea 18 of the eye is enlarged. Without this diverging lens 13 the working distance which is necessary for the pupil imaging would correspond approximately to the distance $S_o$ between the surface 3' of the lens system 3 facing the intermediate image plane 5. By the addition of the diverging lens system 13 the beams of rays 17 are bundled in a distance S, being a focal length of the ophthalmoscope, upstream of the first lens system, which is larger than $S_o$ by a value $\Delta S$. Thus, a larger working distance A between the surface 3" of the converging lens 3 facing the eye 1 and the cornea 18 of the eye is resulting. Such an enlarged working distance A allows an observer of the eye 2 to move the ophthalmoscope without any restriction of the nose or frontal bone in front of the eye 1.

Figure 4:
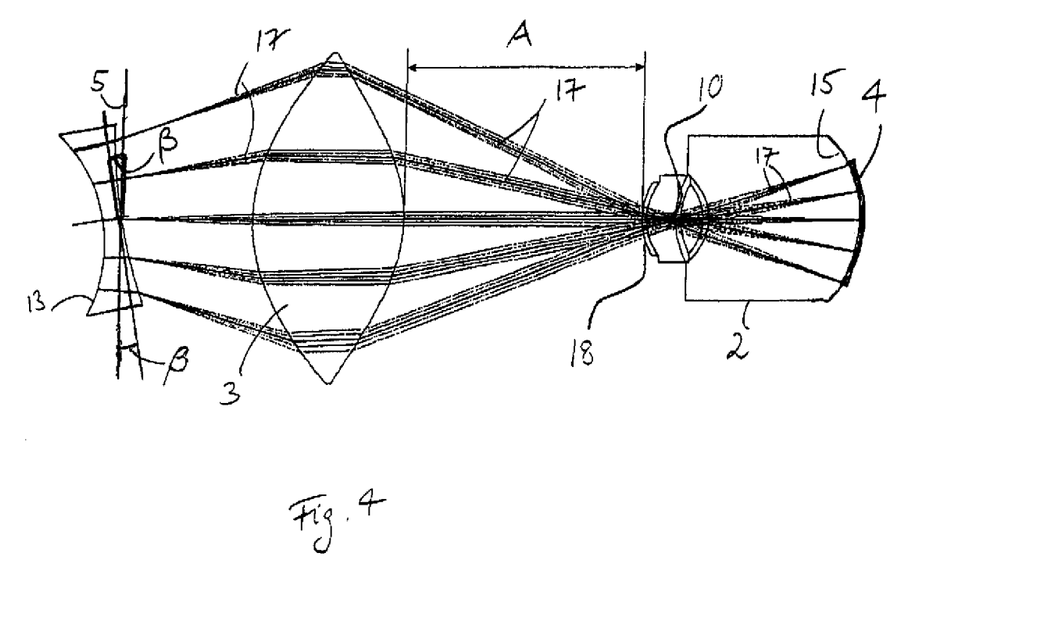
FIG. 4 shows an ophthalmoscope of the type proposed herein with a lens tilted relative to the intermediate image plane.

In FIG. 4, in turn a section of a specific embodiment of an ophthalmoscope of the type herein presented is represented in section and schematically. The difference to the ophthalmoscope described according to FIG. 3 is the tilting of the diverging second lens system 13 relative to the intermediate image plane 5 by an angle β. In the present case the angle β of tilting is 9.5°. The tilting has the positive effect of an elimination of reflections of light from the beam path of the ophthalmoscope such that the reflections of light might not lead to a degradation of image quality of an image of the region 4.

Figure 5:
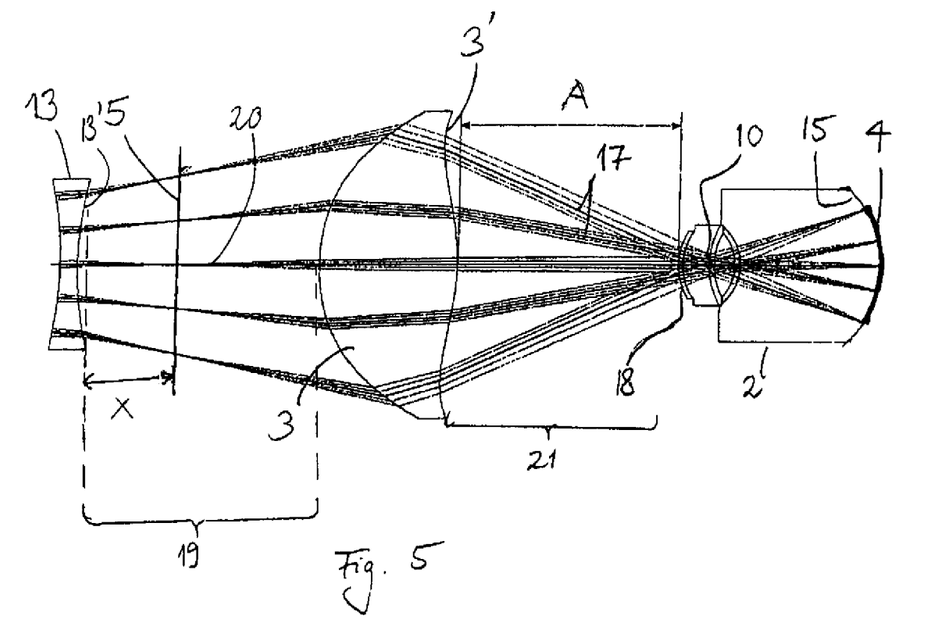
FIG. 5 shows an ophthalmoscope of the type proposed herein with an intermediate image plane in a first interstice between the first and the second lens system.

Again, in FIG. 5 a specific embodiment of the ophthalmoscope of the type proposed here is represented in section and schematically. Unlike the embodiments described according to the FIG. 1 to FIG. 4 in this case the intermediate image plane 5 is arranged in a first interstice 19 between the first lens system 3 and the second lens system 13. A distance X between the intermediate image plane 5 and a surface 13' of the second lens system 13 facing the intermediate image plane 5 is about 2 mm in the present embodiment. This is advantageous in that in the case of laser treatment of the fundus 15 of the eye of the eye 2 a radiation power inside of the second lens system 13 is reduced compared to the radiation intensity inside of the intermediate image plane 5. Furthermore, the surface is shaped aspherically. Further, in an intermediate region 21 between the first lens system 3 and the eye 2 any other mirrors, beam splitters, or lenses are not provided.

Figure 6:
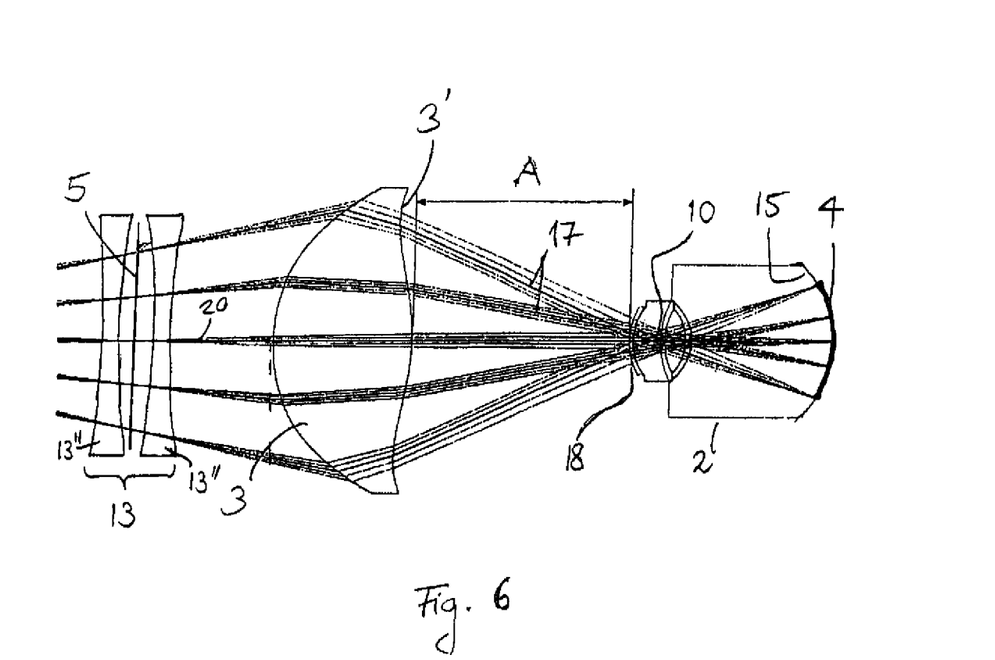
FIG. 6 shows an ophthalmoscope of the type proposed herein with an intermediate image plane inside of the second lens system.

In FIG. 6 another embodiment of an ophthalmoscope of the type proposed herein is represented in section and schematically. Unlike the ophthalmoscope described according to FIG. 5, the second lens system 13 of this embodiment comprises two diverging lenses 13". The intermediate image plane 5 is arranged in intermediate region between the both diverging lenses 13" inside of the second lens system 13. Its advantage is in turn the reduction of radiation power inside of the diverging lenses 13" of the second lens system 13 for the protection of these lenses 13" against a too high radiation intensity, for example in the case of a laser treatment of the fundus 15 of the eye.

The distances $S_o$, $\Delta S$, $S$, and $X$ are each defined along an optical axis 20 of the ophthalmoscope.

Thus, the present invention is an ophthalmoscope for the observation of an eye, in particular of a fundus of the eye, by which a large working distance and large field angle may be achieved but wherein the construction length of the ophthalmoscope is as compact as possible, and wherein at the same time good pupil imaging is achieved. Furthermore, high image quality is achieved with a small sensor.

The ophthalmoscope according to the invention for observing an eye comprises a converging (positively refracting) first lens system for generating a real intermediate image of a region in the eye in an intermediate image plane as well as an observation apparatus having imaging optics for imaging the real intermediate image in an imaging plane in the observation apparatus, and for imaging an aperture of the observation apparatus in a pupil of the eye wherein between the first lens system and the imaging optics a diverging (negatively refracting) second lens system is provided for enlarging a working distance between the first lens system and the pupil, and for enlarging a field angle.

The first lens system comprises at least one converging (positively refracting) lens, and furthermore the second lens system comprises at least one diverging (negatively refracting) lens. Both lens systems may also comprise further lenses.

By a converging (positively refracting) lens system a system of at least one lens is to be understood which converges a beam of rays of light beams running parallel to each other and passing through the positively refracting lens system. By a negatively refracting lens system a system of at least one lens is to be understood which refracts and diverges such a beam of rays passing this lens system.

By the arrangement of the diverging second lens system according to the invention it is achieved that the working distance necessary for achieving the pupil imaging is enlarged, wherein the working distance is defined as above by a distance between the cornea of the eye and a surface facing the eye of an entrance lens of the first lens system facing the eye. In particular, the working distance being achievable by the invention is larger than the distance between this surface and a focus of the first lens system facing the eye which corresponds to the working distance of a conventional ophthalmoscope without the second lens system. As already mentioned above, an enlarged working distance is advantageous in that other devices such as a contact lens can easily be placed between the ophthalmoscope and the eye. Further, a larger field angle can be achieved and a larger clearance of motion is made for the ophthalmoscope since particularly the distance to the nose and forehead of the patient will be enlarged as well.

In a further development being distinguished by particularly good optical image characteristics it is provided that the intermediate image plane is arranged inside the second lens system, in a first interstice between the first lens system and the second lens system, or in a second interstice between the second lens system and the imaging optics.

If the second lens system comprises exactly one lens then the intermediate image plane is located inside of the second lens system if the intermediate image plane passes through the respective lens. If the second lens system includes several of lenses then the intermediate image plane is located inside of the second lens system if the intermediate image plane is located between these both lenses or at least is passing through one of these both lenses. The same applies to the first lens system and the imaging optics. The intermediate image plane is in the first interstice between the first and the second lens systems if it is located between a surface of the second lens system facing the first lens system and a surface of the first lens system facing the second lens system, however, is located inside of neither the first nor the second lens systems. The intermediate image plane is in the second interstice between the second lens system and the imaging optics if it is located between a surface of the second lens system facing the imaging optics and a surface of the imaging optics facing the second lens system, however, is located neither inside of the second lens system nor inside of the imaging optics.

In one embodiment it is provided that the second lens system comprises exactly one diverging lens and the intermediate image plane is arranged inside of this lens. By the use of a single diverging lens in the intermediate image plane a working distance larger than usually will be achieved. On the other hand, the focal distance of the first lens system for imaging the intermediate image in the intermediate image plane remains unchanged such that firstly the intermediate image plane is not shifted by the second lens system, and secondly the intermediate image is not enlarged so that there is no need for the imaging optics provided downstream to be adapted to the second lens system.

An alternative embodiment of the ophthalmoscope according to the invention provides that the intermediate image plane in the first interstice is arranged in close vicinity to a surface of the second lens system facing the first lens system or that the intermediate image plane in the second interstice is arranged in close vicinity to a surface of the second lens system facing the imaging optics. In this way, a radiation power inside of the second lens system can be reduced. In particular, upon laser treatment of the eye this is advantageous in that the second lens system is protected from excessive radiation intensity of the laser which inside of the intermediate image plane is higher than usual. Especially for the treatment of the fundus of the eye a therapeutic laser beam is namely focused onto the fundus of the eye to achieve a radiation power in the fundus of the eye as high as possible. Focusing laser beam onto the fundus of the eye simultaneously means focusing the laser onto the intermediate image plane.

In order to simultaneously achieve a working distance as large as possible between the eye and the first lens system, not to change the position of the intermediate image plane, and if possible not to enlarge the intermediate image, in one embodiment it is provided that the intermediate image plane in the first interstice is arranged in a distance of 1 mm to 20 mm toward a surface of the second lens system facing the first lens system or that the intermediate image plane in the second interstice is arranged in a distance of 1 mm to 20 mm toward a surface of the second lens system facing the imaging optics. In another embodiment the mentioned distance is between 5 millimetres and 15 millimetres.

An embodiment of the ophthalmoscope of the type represented herein provides that the second lens system comprises at least two lenses wherein the intermediate image plane is arranged in an interstice between the at least two lenses. Again, in this way a reduction of a radiation power of a therapeutic laser beam inside of this lens material of the second lens system can be made, and at the same time a large working distance can be achieved.

In another configuration of the invention at least one lens contained in the second lens system is tilted relative to the intermediate image plane. In this way, an amount of stray light can be eliminated from the observation beam, and imaging quality of the ophthalmoscope can be improved. Preferably, a corresponding rotational angle between the tilted lens and the intermediate image plane is in a range between 0° and 45°. In a further development the rotational angle is within a range between 5° and 15°. Alternatively or additionally also lenses contained in the first lens system may be tilted accordingly.

In an embodiment of the invention, there is provided that the first lens system comprises a lens having a curved surface wherein the surface is formed aspherically. This is for the purpose of an optimization of the pupil imaging and the fundus imaging by means of a number as small as possible of optical surfaces. Such an optimization is particularly advantageous by means of aspherical surfaces since aspherical shaping of the lens surface allows a local optimization for every viewing angle. In doing so, local radii of curvature of the aspherical surfaces may be adapted according to an entrance height of a beam of rays. Here, the entrance height of the beam of rays is defined as the distance between a symmetry axis (relative to a rotational symmetry) of the lens and an entrance point of the beam of rays into the lens.

Optimization of imaging characteristics of the ophthalmoscope by means of aspherical lens surfaces compared with optimization by means of additional spherical lenses has the advantage of saving additional lens surfaces (optical surfaces) and thus of avoiding additional reflections of light on these surfaces.

In an alternative embodiment of the invention it is provided that the second lens system comprises a lens having a curved surface wherein this surface is shaped aspherically. In turn, aspherical shaping this lens is for the purpose described above. In a preferred embodiment the first and the second lens systems each comprise a lens having such an aspherically shaped surface.

In a further development of the invention it is provided that the observation apparatus comprises a light sensitive sensor which is arranged in the image plane for generating electric image signals. Such a sensor is applicable to allow digital image processing. Such an ophthalmoscope equipped with digital image processing offers a plurality of auxiliary diagnostic functions which shall not be further explained in detail herein.

An advantageous embodiment of the ophthalmoscope provides that the ophthalmoscope does not include any mirror, beam splitter, and/or any other lens in the intermediate region between the first and the second lens systems. In this way, a construction as simple and cost-effective as possible is feasible which furthermore is distinguished by a particularly high image quality since a reduction of stray light and unwanted reflections of light will be achieved by saving optical surfaces. For the same reason another embodiment of the invention provides that the ophthalmoscope does not comprise any mirror, beam splitter, and/or any other lens in an interstice between the eye and the first lens system.

An especially simple embodiment of the invention which is distinguished by a high imaging quality and a low amount of stray light provides that in addition to imaging of the region in the eye in the intermediate image plane and in the imaging plane no further imaging of the eye is provided.

The method of observing an eye according to the invention with an ophthalmoscope of the type represented herein provides that an observation beam reflected in the eye is imaged by a first lens system of the ophthalmoscope as an intermediate image in an intermediate image plane and the intermediate image is imaged by imaging optics of an observation apparatus of the ophthalmoscope in an imaging plane wherein the observation beam is diverged in a beam path between the first lens system and the imaging optics by a second lens system, and wherein furthermore an aperture of the observation apparatus is imaged in a pupil of the eye. In one embodiment this method is carried out with an ophthalmoscope of the type proposed herein.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

The invention claimed is:

1. An ophthalmoscope for observing an eye, the ophthalmoscope comprising
    a converging first lens system configured to generate a real intermediate image of a region in the eye in an intermediate image plane;
    an observation apparatus having imaging optics configured to image the real intermediate image in an imaging plane in the observation apparatus and configured to image an aperture of the observation apparatus in a pupil of the eye; and
    a diverging second lens system between the first lens system and the imaging optics of the observation apparatus, the diverging second lens system configured to enlarge a working distance between the first lens system and the pupil and/or to enlarge a field angle.

2. The ophthalmoscope of claim 1, wherein the intermediate image plane is arranged inside of the second lens system, in a first interstice between the first lens system and the second lens system, or in a second interstice between said second lens system and said imaging optics.

3. The ophthalmoscope of claim 2, wherein the intermediate image plane is arranged in the first interstice proximate to a surface of the second lens system facing the first lens system.

4. The ophthalmoscope of claim 3, wherein the intermediate image plane is arranged in the first interstice at a distance of 1 mm to 20 mm to the surface of the second lens system facing the first lens system 5. The ophthalmoscope of claim 2, wherein the intermediate image plane is arranged in the second interstice proximate to a surface of the second lens system facing the imaging optics.

6. The ophthalmoscope of claim 2, wherein the intermediate image plane is arranged in the second interstice at a distance of 1 mm to 20 mm to the surface of the second lens system facing the imaging optics.

7. The ophthalmoscope of claim 1, wherein the second lens system consists of a diverging lens and the intermediate image plane is arranged inside of the diverging lens.

8. The ophthalmoscope of claim 1, wherein the second lens system comprises a diverging lens tilted relative to the intermediate image plane.

9. The ophthalmoscope of claim 1, wherein the diverging lens is tilted relative to the intermediate image plane by an angle in a range between 0° and 45°.

10. The ophthalmoscope of claim 1, wherein the first lens system comprises a lens having a curved surface that is aspherically shaped.

11. The ophthalmoscope of claim 1, wherein the second lens system comprises a lens having a curved surface that is aspherically shaped.

12. The ophthalmoscope of claim 1, wherein the observation apparatus comprises a light sensitive sensor arranged in the imaging plane and configured to generate electric image signals.

13. The ophthalmoscope of claim 1, wherein the imaging of the region in the eye is the only image provided in the intermediate image plane.

14. The ophthalmoscope of claim 1, wherein the ophthalmoscope is configured to observe a fundus of the eye.

15. The ophthalmoscope of claim 1, wherein the imaging optics of the observation apparatus comprises a converging third lens system, wherein the aperture of the observation apparatus is arranged between the converging third lens system of the imaging optics of the observation apparatus and the imaging plane of the observation apparatus.

16. The ophthalmoscope of claim 15, wherein the converging third lens system of the imaging optics of the observation apparatus is configured to focus the real intermediate image to infinity.

17. The ophthalmoscope of claim 16, wherein the imaging optics of the observation apparatus comprises a converging fourth lens system, wherein the converging fourth lens system is arranged between the aperture and the imaging plane of the observation apparatus, wherein the converging fourth lens system is configured to focus the real intermediate image onto the imaging plane of the observation apparatus.

18. A method for observing an eye with an ophthalmoscope, the method comprising:
    reflecting an observation beam in the eye to generate an intermediate image of a region in the eye in an intermediate image plane within the ophthalmoscope with a first lens system of the ophthalmoscope;
    imaging, with an imaging optics of an observation apparatus of the ophthalmoscope, the intermediate image in an imaging plane in the observation apparatus;
    diverging the observation beam in a beam path between the first lens system and the imaging optics by a second lens system of the ophthalmoscope; and
    imaging, with the imaging optics of the observation apparatus, an aperture of the observation apparatus in a pupil of the eye.

19. The method of claim 18, wherein the diverging step comprises:
    enlarging a working distance between the first lens system and the pupil; and
    enlarging a field angle of the ophthalmoscope.

20. The method of claim 18, wherein the imaging optics of the observation apparatus comprises a third lens system, wherein the aperture of the observation apparatus is arranged between the third lens system of the observation apparatus and the imaging plane of the observation apparatus.

21. The method of claim 20, the method further comprising:
    focussing the real intermediate image to infinity by the third lens system of the imaging optics of the observation apparatus.

22. The method of claim 21, further comprising:
    focussing the real intermediate image onto the imaging plane of the observation apparatus by a fourth lens system of the imaging optics of the observation apparatus, wherein the fourth lens system is arranged between the aperture and the imaging plane of the observation apparatus.

* * * * *